United States Patent [19]
Bar-Or et al.

[11] Patent Number: 5,702,351
[45] Date of Patent: Dec. 30, 1997

[54] LARYNGOSCOPE AND DISPOSABLE BLADE THEREFOR

[76] Inventors: David Bar-Or, 900 E. Oxford La., Englewood, Colo. 80110; James S. Kimmel, 2566 E. Geddes Pl., Littleton, Colo. 80122; Francis A. Roth, 10945 W. 66th Ave., Arvada, Colo. 80004

[21] Appl. No.: 559,427

[22] Filed: Nov. 15, 1995

Related U.S. Application Data

[60] Provisional application No. 60/002,698, Aug. 23, 1995.

[51] Int. Cl.⁶ .................................................. A61B 1/26
[52] U.S. Cl. .................... 600/190; 600/185; 600/187; 600/193; 600/237
[58] Field of Search ....................... 600/185, 187, 600/188, 190, 193, 194, 197, 237, 240, 241

[56] References Cited

U.S. PATENT DOCUMENTS

| | | | |
|---|---|---|---|
| 4,126,127 | 11/1978 | May | 600/187 |
| 4,930,495 | 6/1990 | Upsher | 600/193 |
| 5,347,995 | 9/1994 | Slater et al. | |
| 5,355,870 | 10/1994 | Lacy | |
| 5,363,840 | 11/1994 | Silva | |
| 5,381,787 | 1/1995 | Bullard | |
| 5,390,663 | 2/1995 | Schaefer | |
| 5,394,865 | 3/1995 | Salerno | |
| 5,400,771 | 3/1995 | Pirak et al. | |
| 5,402,771 | 4/1995 | Pilling | |
| 5,406,941 | 4/1995 | Roberts | |
| 5,419,319 | 5/1995 | Werner | |
| 5,421,325 | 6/1995 | Cinberg et al. | |
| 5,425,356 | 6/1995 | Ough | |

FOREIGN PATENT DOCUMENTS

| | | | |
|---|---|---|---|
| 9403101 | 2/1994 | WIPO | 600/193 |

*Primary Examiner*—Richard J. Apley
*Assistant Examiner*—Beverly M. Flanagan
*Attorney, Agent, or Firm*—Timothy J. Martin

[57] ABSTRACT

A disposable laryngoscope blade connects to a handle especially to facilitate endotracheal intubation of a patient. The blade includes a base portion that attaches to the handle, and an elongated blade portion extends from a proximal end to terminate in a distal tip. The blade portion is arcuate and flattened so as to have a flat upper wall and a flat lower wall joined at lateral edges, and the lateral edges converge toward the distal tip. The blade includes a passageway therethrough so that a vacuum source may attach to a nipple near the proximal end and an inlet port is formed near the distal tip so that fluids may pass through the blade portion. The handle carries a battery power source and electrical contacts. The base portion of the blade also has contacts so that, when the blade is mounted a circuit is completed to power a light source disposed on the blade portion. The blade is preferably formed of two separate plastic pieces joined along a plane perpendicular to the flat upper and lower surfaces of the blade portion to create a housing for the light source and its electrical leads as well as the fluid flow passageway. The base portion has a breakaway latch that engages a notch in the handle so that removal of the blade from the handle breaks the latch structure thereby inhibiting reattachment to the handle.

22 Claims, 3 Drawing Sheets

Fig.2

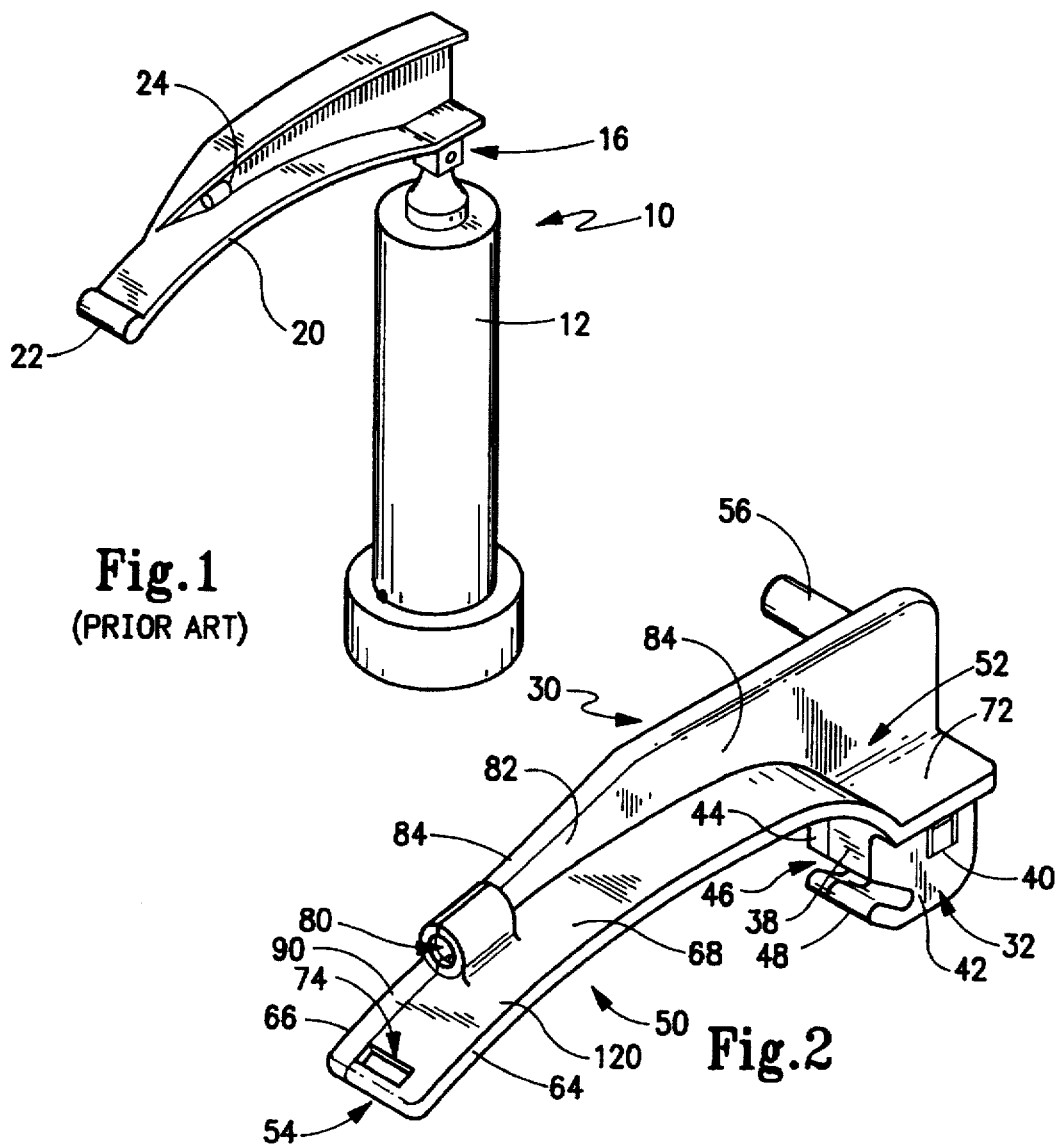
Fig.1 (PRIOR ART)
Fig.2
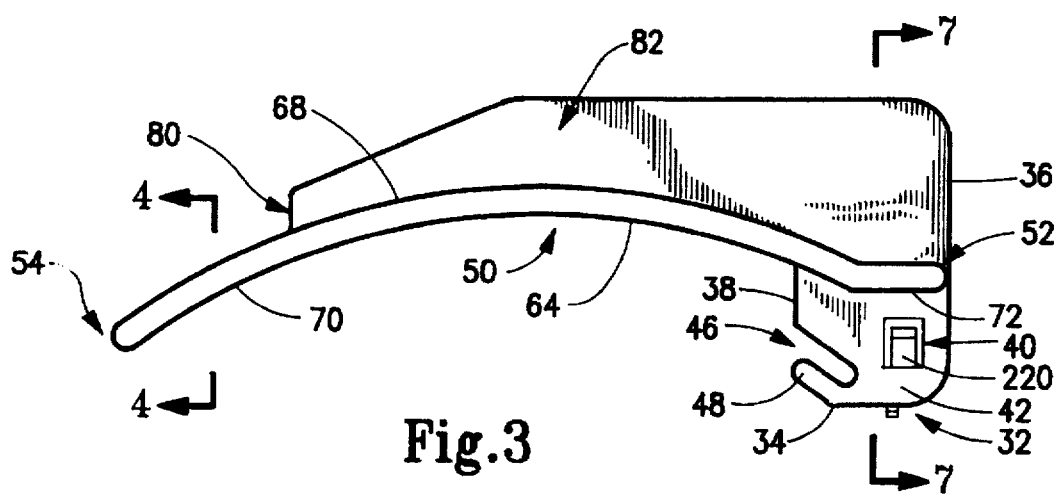
Fig.3

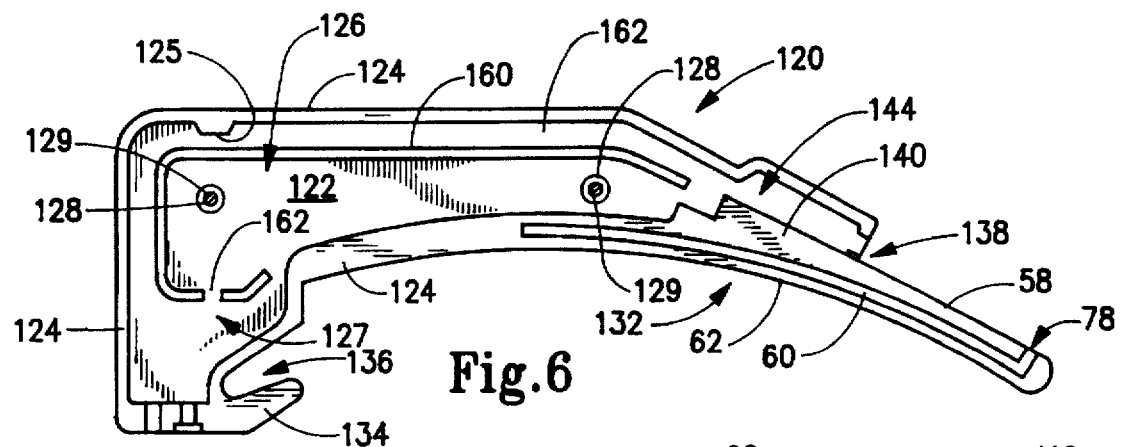
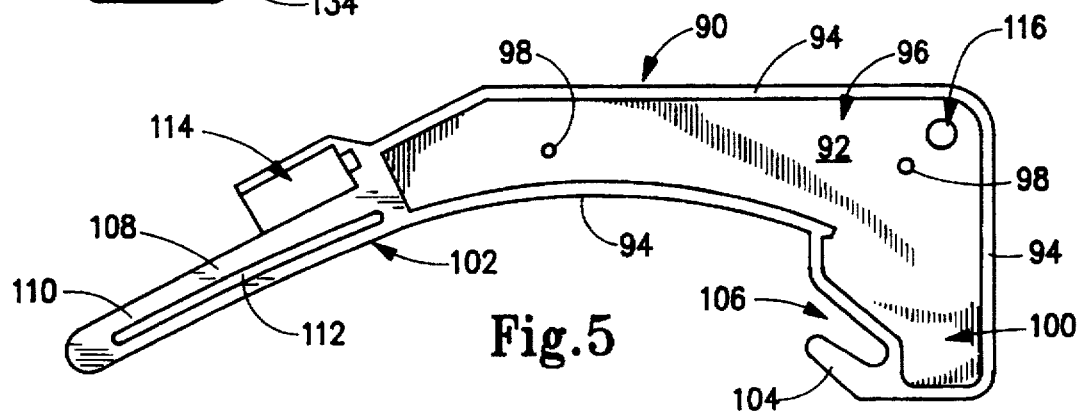
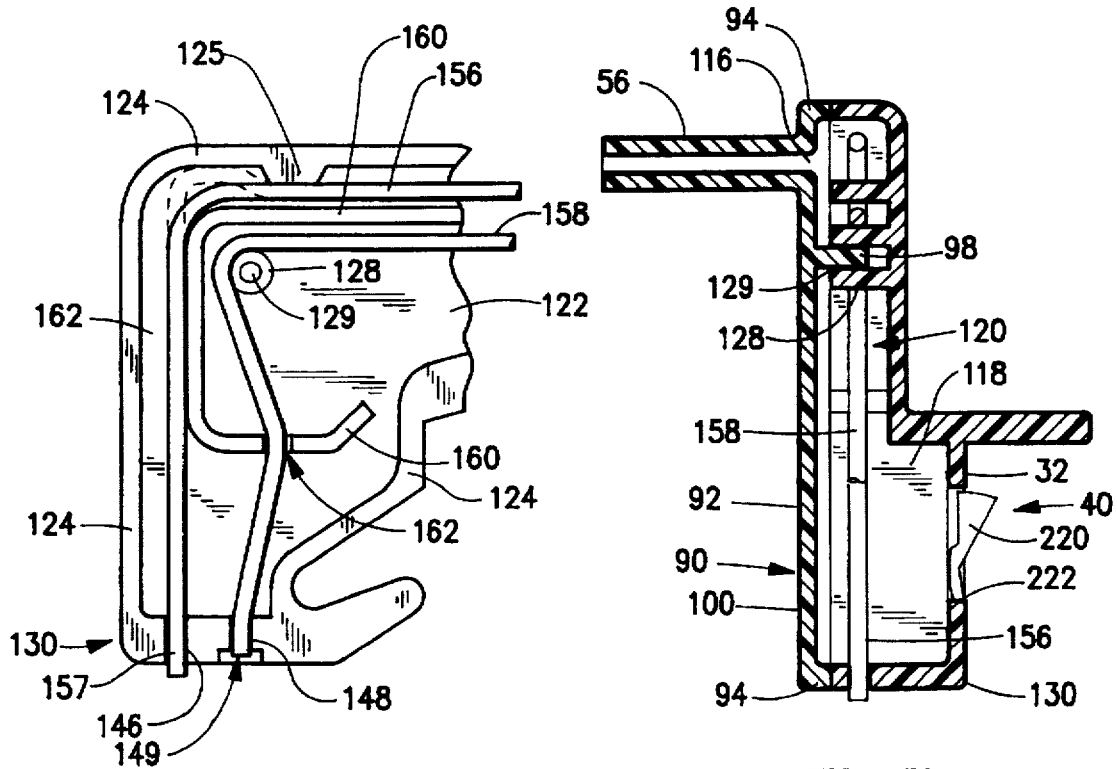

ns
5,702,351

1

LARYNGOSCOPE AND DISPOSABLE BLADE THEREFOR

RELATED APPLICATION

This application is a continuation-in-part of our provisional application Ser. No. 60/002,698, filed Aug. 23, 1995.

FIELD OF THE INVENTION

The present invention generally relates to the field of medical devices that are used during medical treatment, such as surgery. More particularly, the present invention relates to those devices known as laryngoscopes which are used to facilitate endotracheal intubation of a patient to permit the administration of anesthesia. This invention particularly concerns a laryngoscope and a blade therefor which blade is disposable.

BACKGROUND OF THE INVENTION

The treatment and care of patients having injuries or disease entities is of major concern to virtually every society. Often, visualization of the interior of the larynx is important for diagnostic purposes, and the manipulation of the interior of the larynx is often used in therapeutic and surgical procedures. A laryngoscope is a device used by a physician to perform these diagnostic, therapeutic and surgical procedures. A laryngoscope typically comprises a handle that accommodates a removable blade which serves a tongue depressor. A light may be carried on the blade, with the blade having a pair of contacts which connect to cooperative electrical contacts on the handle. The handle is then provided with a source of electrical power, such as a battery supply, so that a distal tip of the laryngoscope blade is illuminated.

Laryngoscopes are widely used during a process called endotracheal intubation of a patient. Endotracheal intubation is a procedure used to provide a patient with a positive air passageway either for the administration of anesthesia or for the mechanical ventilation of the lung's of the patient. In the human anatomy, the epiglottis normally overlies the glottis opening into the larynx to prevent the passage of food into the trachea during eating. Therefore, in endotracheal intubation, it is necessary to displace the epiglottis from the glottis opening to permit the endotracheal air tube to be inserted into the trachea. Displacement of the epiglottis, then, is accomplished by the laryngoscope blade.

A standard laryngoscope employs a stainless steel handle which often carries one or more batteries as an electrical power source. A stainless steel blade has a proximal end which may be releaseably secured to the handle so as to make electrical connection with the power source. The laryngoscope blade terminates in a distal tip, and substantially the entire blade of the laryngoscope is insertable into the patient's throat through the oral opening. As noted, a light source may be provided to illuminate the interior of the patient's mouth and throat for viewing and to facilitate proper insertion of the endotracheal tube. The laryngoscope blade is also constructed of stainless steel, and may take either a flattened or arcuate configuration.

Due to the contact of the laryngoscope blade with bodily fluids, a risk is involved in the re-use of the equipment absent complete sterilization. Sterilization must be accompanied by thorough scrubbing to remove all solid particulate contaminants from the various contours and crevices of the laryngoscope blade as well as from around the light source structure and the blade/handle connective joint. This sterilization procedure is difficult at best, and the difficultly of sterilization is exacerbated since heat generated by the light source can dehydrate fluids that have coated the bulb thereby causing them to harden and become exceedingly difficult to remove.

Indeed, it has been found that residue from previous procedures may sometimes remain on the laryngoscope blade, especially in the light bulb region, even after sterilization. Therefore, various infectious disease entities may not be killed or removed by normal sterilization procedures. In many medical emergencies, even typical sterilization techniques are unavailable. Mobile trauma units, such as emergency medical vehicles, helicopters and airplanes, simply cannot carry sterilization equipment along with their array of rescue and treatment apparatus.

In an effort to eliminate cross-contamination between patients where laryngoscopes are employed, it has been known to provide a laryngoscope blade with a single use, disposable, prophylactic covering. For example, U.S. Pat. No. 5,347,995 issued Sep. 20, 1994 to Maraglio et al provides a disposable laryngoscope blade cover that has a flexible sleeve and a resilient slide band. The slide band is attached to the sleeve and engages the handle of the laryngoscope to maintain the sleeve on the laryngoscope blade. This disposable blade cover, as well as other disposable covers known in the art, are difficult to use and, in some instances, are quite expensive.

Moreover, it is often the case that bodily fluids, such as blood and vomit, interfere with endotracheal intubation. These fluids may obstruct visualization of the vocal cords and may scatter the light produced by the light source thereby decreasing visibility. In these situations, the attending physician or anesthesiologist often must employ a separate suction device to remove the aforementioned fluids. The use of an additional device necessitates the use of both hands, thus slowing the endotracheal intubation procedure. Often, by the time the suction tip device is removed, the fluids may have again accumulated.

As a result, it is known to provide an intubator device with an internal suction channel. For example, as is shown in U.S. Pat. No. 5,287,848 issued Feb. 22, 1994 to Cubb et al, an intubator may be provided with an internal channel for receiving the endotracheal tube, a separate channel for the insertion of a fiber optic light source, and a third channel which may be used for the suctioning of fluids from the throat of the patient. The device shown in the '848 Patent, however, is fairly bulky for insertion into the patient and is somewhat complex in structure. Further, should a device such as shown in the '848 Patent be desired for re-use, it would be impossible to use a disposable protective sleeve, of the type described above, since such sleeve would block the suction passageway and interfere with the illumination provided by the light source.

Accordingly, there remains a need for improved laryngoscopes and blades therefor. A specific need has arisen for the construction of a disposable laryngoscope blade which can be produced at low cost so that it may be discarded after use thereby avoiding the need for sterilization. A further need exists for disposable laryngoscope blades which are easy to use and which provide both a suction source and a light source in a single device.

SUMMARY OF THE INVENTION

It is an object of the present invention to provide a new and useful laryngoscope and, specifically, an improved laryngoscope blade therefor, which is relatively inexpensive to produce so that it may be disposable.

Another object of the present invention is to provide a laryngoscope and a blade therefore which can be injection molded out of inexpensive plastic materials.

A further object of the present invention is to provide a laryngoscope blade that includes a light source and is structured so as to provide suction for the removal of fluids from a patient's throat during use.

Yet another object of the present invention is to provide a laryngoscope blade which provides a passageway which may be employed when attached to a suction source to remove fluids from a patient's throat but which also may be used to introduce medications to the patient during endotracheal intubation.

It is a further object of the present invention to provide a laryngoscope blade with a one-shot frangible latch structure to discourage reattachment of laryngoscope blade after removal from the handle.

According to the present invention, then, a laryngoscope is provided with a new and useful laryngoscope blade. The laryngoscope blade is adapted for connection to a handle and to a vacuum source and may be inserted into the throat of a patient to facilitate endotracheal intubation. The laryngoscope blade includes a blade portion which is sized and configured for attachment to a laryngoscope handle. The blade includes an elongated blade portion that has a proximal end connected to a base portion and which projects from the base portion to terminate in a distal tip. The blade portion includes a passageway formed therein, and an inlet port is in fluid communication with the passageway and is located proximately to the distal tip. An outlet port is also in fluid communication with the passageway and is located proximately to the proximal end of the blade portion. The outlet port includes a connector structure that is configured to connect a vacuum source whereby suction may be provided at the distal tip to remove fluid from the patient through the blade portion.

The laryngoscope blade also includes a light source disposed on the blade portion which light source is operative to illuminate the distal tip. Here, the handle portion includes an electrical power source, such as batteries, and the handle is provided with first electrical contacts. The base portion of the laryngoscope blade is provided with second electrical contacts that are electrically connected to the light source and the first and second electrical contacts are positioned so that they will make electrical connection when the base portion is attached to the handle. Preferably, a light source housing is formed by walls that are integral extensions of the blade portion, and the light source housing encloses and seals the light source from fluids in the patient's throat.

In its preferred construction, the blade portion of the laryngoscope blade has a flat upper wall and a flat lower wall spaced from the flat upper wall thereby to form a section of the passageway with the blade portion having an upper surface and a lower surface. The upper and lower walls are joined along a pair of lateral side edges, and these lateral side edges preferably converge toward one another in a direction from the proximal end to the distal tip so that the blade portion is tapered in width. With this construction, the inlet port is formed through the upper wall at a region adjacent the distal tip. Preferably the laryngoscope blade is formed by first and second pieces fabricated of a plastic material and joined to one another along a plane that is perpendicular to the upper and lower surfaces of the blade portion so that a section of each of the blade and base portions are formed by each of the first and second pieces. When the first and second pieces are joined, they enclose an open interior that forms the passageway. The connector structure may include a nipple formed on the first piece, and the upper and lower walls of the blade portion are formed by the second piece.

Further, it is preferred that the laryngoscope blade of the present invention include a frangible latch member which engages the handle when the blade is connected thereto in a mounted state. This frangible latch is constructed to break upon removal of the blade from the handle thereby to inhibit reconnection of the blade to the handle. For example, the laryngoscope according to the present invention may include a handle which is adapted to be manually grasped by a user and includes a first connector and a first latch element. The disposable laryngoscope blade includes a base portion provided with a second connector that is operative to selectively mount the blade in a mounted state to the handle with the elongated blade portion projecting therefrom. The base portion has a frangible second latch element that is operative to cooperatively engage the first latch element. The first latch element may be defined by a notch in the handle and the second latch element may be formed by a stiff yet resilient tooth oriented to engage the notch when the blade is in the mounted state. Removal of the laryngoscope blade after initial connection to the handle breaks this tooth away from the base portion.

These and other objects of the present invention will become more readily appreciated and understood from a consideration of the following detailed description of the exemplary embodiment when taken together with the accompanying drawings, in which:

BRIEF DESCRIPTION OF THE DRAWINGS

FIG. 1 is a perspective view of a laryngoscope according to the prior art;

FIG. 2 is a perspective view of a laryngoscope blade according to the exemplary embodiment of the present invention;

FIG. 3 is a side view in elevation of the laryngoscope blade shown in FIG. 2;

FIG. 5 is a side view in elevation of a first molded plastic piece used to construct the laryngoscope blade shown in FIGS. 2 and 3;

FIG. 6 is a side view in elevation of a second molded plastic piece used to construct the laryngoscope blade of FIGS. 2 and 3;

FIG. 7 is a cross-sectional view taken about lines 7—7 of FIG. 3;

FIG. 8 is an enlarged view of the proximal end portion of the molded plastic piece of FIG. 5 showing the mounting of the electrical wires for the light source therein;

DETAILED DESCRIPTION OF THE EXEMPLARY EMBODIMENT

Figure 9:
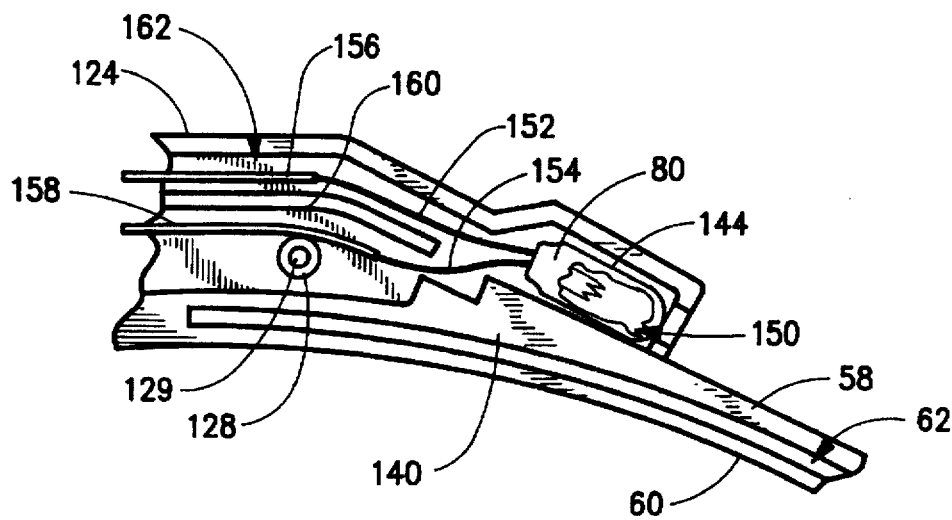
FIG. 9 is an enlarged view of a medial portion of the first molded plastic piece of FIG. 5 showing with the electrical wires and light source mounted therein.

The present invention is directed to a new and useful laryngoscope blade adapted for attachment to a battery powered handle to form a new and useful laryngoscope. The present invention specifically recognizes the need for a disposable laryngoscope blade which is relatively inexpensive to manufacture and which, due to its disposability, avoids the need for repeated sterilization and the dangers of cross contamination between patients which may accompany inadequate sterilization. Broadly, the present invention provides a laryngoscope blade which is molded, in two part construction, out of a plastic material such that the laryngoscope blade has the ability to withdraw fluids from the throat of a patient when the blade is connected to a vacuum source or which allows the introduction of medication to the patient during endotracheal intubation. The laryngoscope blade also provides a light source to eliminate the distal tip of the blade during use.

Laryngoscopes, and laryngoscope blades, have been widely known in the past. For example, the typical prior art laryngoscope is shown for background purposes in FIG. 1 where it may be seen that laryngoscope 10 includes a handle 12 that is adapted to manually grasped by a user, such as an attending physician or an emergency medical personnel. Handle 12 may be connected to an electrical power source, but typically contains its own power source in the form of suitable batteries (not shown). A laryngoscope blade 14 is mounted to handle 12 at a connective joint 16. The laryngoscope blade 14 is preferably of solid, stainless steel construction and includes a base portion 18 at a proximal end thereof for attachment at the connective joint 16 and an arcuate blade portion 20 which projects away from base portion 18 to terminate in a distal tip 22. Blade 14 is generally wedge-shape in appearance and is oriented at generally a right angle to handle 12 when mounted thereon. A light source 24 is disposed along an upper surface of blade portion 20, an electrical connections (not shown) interconnect light source 24 to the electrical power source in handle 12 through contacts formed in connective joint 16.

While the laryngoscope 10 shown in FIG. 1, and specifically the laryngoscope blade 14, is a very useful medical device, it nonetheless has specific drawbacks. Most notably among these is the difficulty to sterilize the laryngoscope blade due to the various contours and crevices formed, for example, by the structure at its proximal end adjacent connective joint 16 and around light source 24. Even vigorous scrubbing and heat treatments do not always remove the contaminates from laryngoscope blade 14 so that reuse always introduces the danger of contamination to a subsequent patient where the laryngoscope is used after an earlier procedure on a previous patient. Further, where it is necessary to remove fluids such as blood, saliva and/or vomit from the throat of the patient who is receiving endotracheal intubation that is implemented by the laryngoscope 10, a separate suction device must be employed.

According to the present invention, a disposable laryngoscope blade 30 is provided, with the structure of laryngoscope blade 30 being best shown in FIGS. 2–7. With references to FIGS. 2 and 3, it may be seen that laryngoscope blade 30 includes a base portion 32 that is sized and configured for attachment to a handle, such as handle 12 or, alternatively, to a handle 112 described below. Base portion 32 includes a base wall 34, a back wall 36 oriented at generally right angles to base wall 34, and a front wall 38 which is parallel to and spaced from back wall 36. A break-away latch structure 40, described more thoroughly below, is formed in a sidewall 42, and a second sidewall 44 is located in parallel spaced apart relation from sidewall 42. Base portion 32 includes a transverse channel 46 formed in front wall 38 by a lip 48 to facilitate connection to handles, such as handle 12 or handle 200 described below. Laryngoscope blade 30 includes an elongated blade portion 50 which has a proximal end 52 connected to base portion 32, and blade portion 50 projects from base portion 32 to terminate in a distal tip 54. A connector structure in the form of a nipple 56 that is operative to connect to a vacuum source so that suction may be provided at the distal tip of blade portion 50, as described below, in order to remove fluids from the patient through the blade portion.

Figure 4:
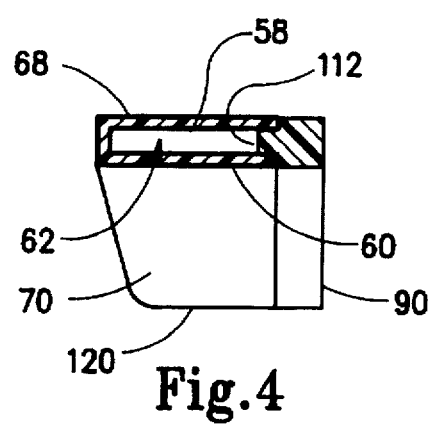
FIG. 4 is a cross-sectional view taken about lines 4—4 of FIG. 3.

Blade portion 50, as is shown in FIGS. 2–4 is formed by relatively flat upper wall 58 and a flat lower wall 60 which are spaced apart from one another and are generally parallel to form a passageway 62 therebetween. While blade portion 50 may take any general configuration known in the art, it is preferred that upper wall 58 and lower wall 60 be arcuate in configuration with a radius similar to the radius of blade portion 20 of laryngoscope blade 14. In any event, upper and lower walls 58 and 60 are joined to one another along a pair of lateral side edges 64 and 66. Blade portion 50 accordingly has an upper surface 68 and a lower surface 70 which are operative to contact the tissue surfaces of the throat of a patient in order to facilitate endotracheal intubation or other medical procedures. Moreover, as is seen in FIGS. 2 and 4, lateral side edges 64 and 66 converge towards one another in a direction from the proximal end 52 toward distal tip 54 so that blade portion 50 tapers in width as measured by the dimension between lateral side edge 64 and 66. Blade portion 50, as is shown in FIG. 3, has a general uniform thickness as measured between upper surface 68 and lower surface 70 and terminates in a ledge 72 located adjacent base portion 32. An inlet port 74 is located at distal tip 54 and is in fluid communication with passageway 62, as is best shown in FIG. 2.

With reference again to FIGS. 2 and 3, it may be seen that the laryngoscope blade 30 includes a light source 80 disposed on blade portion 50 and oriented so that it is operative to illuminate distal tip 54. Light source 80 is enclosed in a light source housing 82 having opposed sidewalls 84 formed as integral extensions of blade portion 50. As described below, light source 82 will connect to the electrical power source in handle 12 by first and second electrical contacts when base portion is in a mounted state on handle 12.

With reference now to FIGS. 5–9, it may now be appreciated that the laryngoscope blade 30 is formed by a first piece 90 and a second piece 120 which are fabricated of a suitable plastic material, such as by injection molding. With reference to FIG. 5, it may be seen that first piece 90 is formed by a flat panel 92 which is surrounded by a rim 94 that extends around the periphery thereof. Thus, rim 94 forms a shallow cavity 96, and a pair of connection posts 98 project upwardly from panel 92. First piece 90 includes a base section 100 and a blade section 102. Base section 100 has a lip structure 104 formed therein to create a channel region 106. A distal portion 108 has an upper surface 110 that is planar with the exposed surface of rim 94. An upright ridge 112 projects outwardly from surface 110, and a cavity 114 is provided to receive the light source 80. Outlet 116 is formed through panel 92 opposite blade section 102.

Second piece 120 is best shown in FIG. 6, and it should be understood that it is configured so as to mate with first piece 90 thereby to form the laryngoscope blade 30. As is shown in FIG. 6, second piece 120 includes a flat panel 122 that is surrounded by a peripheral rim 124 to form a shallow cavity 126 at an upper portion thereof and a deeper cavity 127 at a lower portion thereof. A pair of cup shaped sockets 128 extend outwardly from panel 122, and each includes a bore 129 sized to receive a respective post 98 in mated engagement therewith, as described below. It may further be appreciated that second piece 120 has a base section 130 within which cavity 127 is located and a blade section 132 located at a distal portion of second piece 120. Blade section 132 includes upper wall 58 and lower wall 60, described above with inlet port 78 being formed through upper wall 58. Base section 130 includes a lip structure 134 that defines a channel region 136. A distal portion 138 of second piece 120 includes a flat upper surface 140 which is formed in a common plane with the exposed surface of rim 124. A cavity 144, similar to cavity 104, is provided to receive light source 80.

When assembled, as is best shown in FIG. 2 and 7, rims 94 and 124 abut one another with posts 98 in mated engagement in bores of 129 with sockets 128. Likewise, surface 110 and 140 abut one another with ridge 112 extending partially into passageway 62 (as shown in FIG. 4) thus maintaining the spacing between upper wall 58 and lower wall 62. Cavities 114 and 144 then face one another to form a socket to receive the light source 80. Molded plastic pieces 90 and 120 may be joined to one another in any suitable manner, such as an adhesive, ultrasonic welding, or the like. Joinder occurs, then, along a plane that is perpendicular to upper surface 68 and lower surface 70.

Prior to joining pieces 90 and 120 together, however, it is preferred that the light source 80 be positioned so that the joinder of first and second pieces 90, 120 will suitably enclose the light source. To this end, as is shown in FIGS. 7–10, light source 80 in the form of any suitable light bulb, may be positioned in cavity 144 and, if desired, a disk-shaped lens 150 may be mounted forwardly of light source 80 in a direction towards distal tip 54. Light source 80 includes a pair of electrical leads 152, 154 which are respectively secured, such as soldering, to larger copper leads 156,158, respectively. Leads 156 and 158 are electrically isolated from one another by means of an upstanding ridge 160 which extends outwardly from flat panel 122 and which is generally a reverse J-shape configuration, as is shown in FIG. 6. As is shown in FIG. 8, copper lead 156 extends in a channel 162 located between rim 124 and ridge 160 and terminates light source 80 in an end 157 that is disposed in a first notch 146 and rim 124 at base section 130. As is further shown in these figures, second lead 158 is positioned between sockets 128 and ridge 160 and extends through a gap 162 in ridge 160 and is positioned in a second notch 148 having a countersunk opening 149, with notch 148 being located in base section 130. As may be best seen in FIGS. 6 and 8, rim 124 is provided with a nub 125 that biases wire 156 toward notch 146. However, upon establishing electrical contact, as described below, wire 146 will be bent or deformed to the position shown in phantom in FIG. 8 so that its thickness and resiliency will tend to maintain electrical contact with handle 200.

Moreover, with reference to FIGS. 2, 5 and 7, it may be seen that first piece 90 is provided with an outlet port 116 that is in communication with nipple 56 so that, by virtue of the open interior 118, fluid communication is established from inlet opening 78, through passageway 62, through interior 118 and out outlet 116 by way of nipple 156 so that attachment of a vacuum source to nipple 56 will apply vacuum at inlet port 78 at the distal tip 54 of the laryngoscope blade 30.

Figure 11:
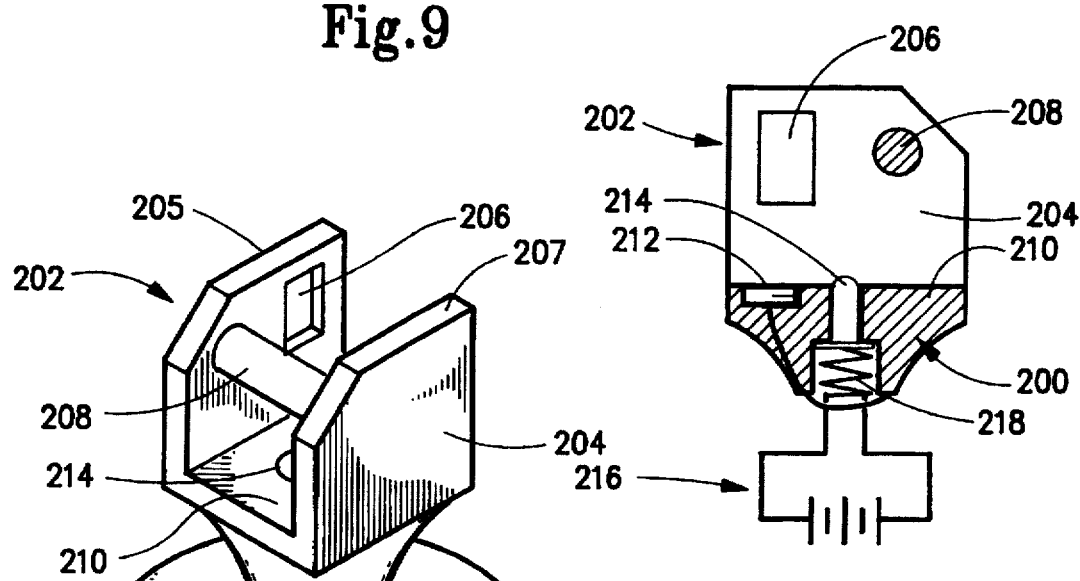
FIG. 11 is a cross-sectional view taken about lines 11—11 of FIG. 9 with a battery power source being shown in diagrammatic format.
Figure 10:
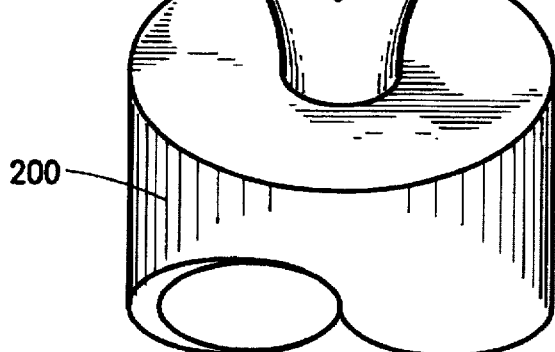
FIG. 10 is a perspective view of the connection joint on a laryngoscope handle according to the exemplary embodiment of the present invention.

Laryngoscope blade 30 is constructed to attach to a handle, such as handle 12, but more preferably to a modified handle 200 best shown in FIGS. 10 and 11. In these figures, it may be seen that handle 200 is provided with a first connector 202 in the form of a pair of spaced apart, parallel walls 204 which are each provided with a notch 206 formed therein. A pin 208 extends transversely between walls 204 at a forward end thereof. As best shown in FIG. 11, base 210 of connector 202 includes first electrical contacts such as plate 212 and spring loaded button 214 which are electrically connected to a battery supply 216. Spring 218 biases button 214 so that it protrudes slightly out of base 210. With reference to FIGS. 2 and 8, it may now be appreciated that, in order to position laryngoscope blade 30 in a mounted state on handle 200, pin 208 is engaged by channel 46 formed by channel regions 106 and 136 such that the lip structure 48 is positioned between pin 208 and base 210. Blade 30 is then rotated to position base wall 34 alongside base 210 with ledge 72 being positioned on an upper edge 207 of wall 204. When this occurs, button 214 is biased by spring 218 into electrical contact with copper cable 158 while plate 212 comes into electrical contact with cable 156 at end 157, thus pushing cable 156 into the deformed position shown in phantom in FIG. 8. As noted above, nub 125 helps maintain the electrical contact of cable 156 with plate 212.

Moreover, a one-shot frangible latch structure 40 engages a selected notch 206 such that notch 206 forms a first latch element and a tooth 220 forms a second latch element which retains laryngoscope blade 30 in the mounted state. With reference to FIG. 7, it may be seen that tooth 220 is a plastic tooth that is molded integraly in base section 130 of second plastic piece 120, and specifically, in wall 32 thereof. Tooth 220 is provided with a fracture line 222 so that, it may only be removed forcibly from connector 202. Upon such forcible removal, the frangible latch member in the form of tooth 220 breaks along fracture line 222 so that blade 30 may not readily be reconnected to the handle 200. That is, breakage of the frangible latch member operates to inhibit reconnection of blade to the handle.

From the foregoing, it should now be appreciated that the present invention provides distinct advantages over previous laryngoscopes and laryngoscope blades therefor. By constructing the laryngoscope blade in the manner described, a reactively inexpensive blade is provided which may be disposable thereby eliminating the need for expensive and sometimes ineffective sterilization processes. This blade structure provides an interior passageway so that a suction source may simultaneously be applied to remove fluids from the throat of a patient during endotracheal intubation and, thereafter, medications may be introduced through outlet port 116, through the interior of the laryngoscope blade 30 and out of inlet port 78 so that the patient may be medicated during the intubation process. The light source 80 illuminates the distal tip during intubation, and lens 50 may either be used simply to seal the cavity which receives light source 80 but also may be used to focus the light beam onto the distal tip 54. Furthermore, by constructing connector 202 in the manner described, with a pair of opposed notches 206, the laryngoscope blade 30 may be made either "left-handed" or "right-handed" by reversing the structure on molded plastic pieces 90 and 120.

Accordingly, the present invention has been described with some degree of particularity directed to the exemplary embodiment of the present invention. It should be appreciated, though, that the present invention is defined by the following claims construed in light of the prior art so that modifications or changes may be made to the exemplary embodiment of the present invention without departing from the inventive concepts contained herein.

We claim:

1. A laryngoscope blade adapted for connection to a handle and a vacuum source for insertion into the throat of a patient and operative to facilitate endotracheal intubation of the patient, comprising:

(a) a base portion sized and configured for attachment to a handle; and (b) an elongated blade portion having a proximal end connected to said base portion and projecting in a longitudinal direction therefrom to terminate in a distal tip, said blade portion having a passageway formed therein with said blade portion including an upper wall and a lower wall that are flat in a direction transverse to the longitudinal direction and that are in generally parallel spaced relationship to one another, said upper wall and said lower wall joined together along lateral side edges thereof to form a section of the passageway that is generally rectangular in cross-section, an inlet port in fluid communication with said passageway and located proximately to the distal tip and an outlet port in fluid communication with said passageway and located proximately to the proximal end, said outlet portion including a connector structure configured to connect to a vacuum source whereby suction may be provided at the distal tip to remove fluids from the patient through said blade portion.

2. A laryngoscope blade according to claim 1 including a light source disposed on said blade portion and operative to illuminate said distal tip.

3. A laryngoscope blade according to claim 2 wherein a handle to which said laryngoscope blade is adapted to connect includes an electrical power source provided with first electrical contacts, said base portion including second electrical contacts electrically connected to said light source, said second electrical contacts positioned on said base portion such that they will make electrical connection to first electrical contacts on a handle when said base portion is attached to a handle.

4. A laryngoscope blade according to claim 2 including a light source housing disposed on said blade portion and enclosing said light source, said light source housing having walls formed as integral extensions of said blade portion.

5. A laryngoscope blade according to claim 1 wherein said lateral side edges converge toward one another in a direction from the proximal end to said distal tip such that said blade portion is tapered in width.

6. A laryngoscope blade according to claim 1 wherein said inlet port is formed through said upper wall.

7. A laryngoscope blade according to claim 1 wherein said base portion and said blade portion are formed by first and second pieces fabricated of plastic material and joined to one another along a plane that is perpendicular to said upper and lower surfaces such that a section of each of said base and blade portions are formed by each of said first and second pieces.

8. A laryngoscope blade according to claim 7 wherein said first and second pieces enclose an open interior when joined thereby to form the passageway, said connector structure including a nipple formed in said first piece.

9. A laryngoscope blade according to claim 8 wherein said upper and lower walls of said blade portion are formed by said second piece.

10. A laryngoscope blade according to claim 1 wherein said base portion includes a frangible latch member which engages a handle when said blade is a connected thereto and constructed to break upon removal of said blade from a handle thereby to inhibit reconnection of said blade to a handle.

11. A laryngoscope blade adapted for connection to a handle and a vacuum source for insertion into the throat of a patient and operative to facilitate endotracheal intubation of the patient, comprising:

(a) a base portion sized and configured for attachment to a handle;

(b) an elongated blade portion having a proximal end connected to said base portion and projecting in a longitudinal direction therefrom to terminate in a distal tip, said blade portion including a passageway formed therein with said blade portion including an upper wall and a lower wall in closely-spaced relation to one another to define a blade thickness and joined together along lateral side edges defining a width for said blade portion in a transverse direction, an inlet port in fluid communication with said passageway and located proximately to the distal tip and an outlet port in fluid communication with said passageway and located proximately to the proximal end, said outlet port including a connector structure configured to connect to a vacuum source whereby suction may be provided at the distal tip to remove fluids from the patient through said blade portion; and (c) said base portion and said blade portion being formed by first and second pieces fabricated of plastic material and joined to one another along a plane that is perpendicular to the transverse direction and to said upper and lower surfaces such that a section of each of said base an blade portions are formed by each of said first and second pieces.

12. A laryngoscope blade according to claim 11 including a socket and a light source disposed in said socket with a section of said socket being formed on each of said base and blade portions.

13. A laryngoscope blade according to claim 12 wherein said light source includes electrical leads associated therewith and wherein one of said first and second pieces includes ridges sized to position and electrically isolate said electrical leads from one another.

14. A laryngoscope blade according to claim 12 including a lens mounted in said socket and operative to focus light from said light source onto the distal tip.

15. A laryngoscope blade according to claim 11 wherein a majority of said blade portion is formed on said first piece.

16. A laryngoscope blade according to claim 15 wherein said connector structure is formed on said second piece.

17. A laryngoscope operative to facilitate endotracheal intubation of a patient, comprising:

(a) a handle adapted to be manually grasped by a user and including a first connector and a first latch element; and (b) a laryngoscope blade including a base portion provided with a second connector operative to selectably mount said blade in a mounted state to said handle and an elongated blade portion having a proximal end connected to said base portion and projecting therefrom to terminate in a distal tip, said blade portion having a passageway formed therein with said blade portion including an upper wall and a lower wall that are flat in a direction transverse to the longitudinal direction and that are in generally parallel spaced relationship to one another, said upper wall and said lower wall joined together along lateral side edges thereof to form a section of the passageway that is generally rectangular in cross-section, an inlet portion in fluid communication with said passageway and located proximately to the proximal end, said outlet portion including a connector structure configured to connect to a vacuum source whereby suction may be provided at the distal tip to remove fluids from the patient through said blade portion.

18. A laryngoscope operative to facilitate endotracheal intubation of a patient, comprising:

(a) a handle adapted to be manually grasped by a user and including a first connector and a first latch element; and (b) a disposable laryngoscope blade including a base portion provided with a second connector operative to selectably mount said blade in a mounted state to said handle and an elongated blade portion having a proximal end connected to said base portion and projecting therefrom to terminate in a distal tip, said blade portion including a passageway formed therein with said blade portion including an upper wall and a lower wall in closely-spaced relation to one another to define a blade thickness and joined together along lateral side edges defining a width for said blade portion in a transverse direction, an inlet port in fluid communication with said passageway and located proximately to the distal tip and an outlet port in fluid communication with said passageway and located proximately to the proximal end, said outlet portion including a connector structure configured to connect to a vacuum source whereby suction may be provided at the distal tip to remove fluids from the patient through said blade portion; and (c) said base portion and said blade portion being formed by first and second pieces fabricated of plastic material and joined to one another along a plane that is perpendicular to the transverse direction and to said upper and lower surfaces such that a section of each of said base and blade portions are formed by each of said first and second pieces.

19. A laryngoscope according to claim 18 wherein said handle includes a first latch element and said base portion includes, a frangible second latch element operative to cooperatively engage said first latch element when said blade is in the mounted state yet operative to break upon removal of said blade from said handle thereby to inhibit remounting of said blade thereon.

20. A laryngoscope according to claim 18 wherein said blade includes a connector structure associated with the outlet port and configured to connect to a vacuum source whereby suction may be provided at the distal tip to remove fluids from the patient through said blade portion.

21. A laryngoscope according to claim 18 wherein said handle includes an electrical power source and is provided with first electrical contacts, said base portion including a second electrical contacts electrically connected to said light source, said second electrical contacts positioned on said base portion such that they will make electrical connection to said first electrical contacts when said base portion is attached to said handle.

22. A laryngoscope according to claim 21 including a light source disposed on said blade portion and operative to illuminate said distal tip portion.

* * * * *